(12) United States Patent
Barrick et al.

(10) Patent No.: US 7,747,312 B2
(45) Date of Patent: Jun. 29, 2010

(54) SYSTEM AND METHOD FOR AUTOMATIC SHAPE REGISTRATION AND INSTRUMENT TRACKING

(75) Inventors: Earl Frederick Barrick, McLean, VA (US); Kenneth J. Hintz, Fairfax Station, VA (US)

(73) Assignee: George Mason Intellectual Properties, Inc., Fairfax, VA (US)

( * ) Notice: Subject to any disclaimer, the term of this patent is extended or adjusted under 35 U.S.C. 154(b) by 1467 days.

(21) Appl. No.: 09/752,557

(22) Filed: Jan. 3, 2001

(65) Prior Publication Data

US 2002/0087101 A1 Jul. 4, 2002

Related U.S. Application Data

(60) Provisional application No. 60/174,343, filed on Jan. 4, 2000, provisional application No. 60/179,073, filed on Jan. 31, 2000.

(51) Int. Cl.
*A61B 5/05* (2006.01)
(52) U.S. Cl. ........................ 600/426; 600/406; 600/407; 600/424; 600/427; 606/130
(58) Field of Classification Search ................. 600/406, 600/407, 424, 427; 606/130
See application file for complete search history.

(56) References Cited

U.S. PATENT DOCUMENTS

| 5,676,673 | A  | * | 10/1997 | Ferre et al. ................... 606/130 |
| 6,127,672 | A  | * | 10/2000 | Danisch ................. 250/227.14 |
| 6,611,700 | B1 | * | 8/2003 | Vilsmeier et al. ........... 600/407 |
| 6,738,656 | B1 | * | 5/2004 | Ferre et al. ................... 600/426 |

OTHER PUBLICATIONS

Measurand, Inc. Web Site: http://www.measurand.com as of Dec. 27, 2000.*

* cited by examiner

*Primary Examiner*—Brian Casler
*Assistant Examiner*—John F Ramirez
(74) *Attorney, Agent, or Firm*—David Grossman

(57) ABSTRACT

There is provided a device for generating a frame of reference and tracking the position and orientation of a tool in computer-assisted image guided surgery or therapy system. A first curvature sensor including fiducial markers is provided for positioning on a patient prior to volumetric imaging, and sensing the patient's body position during surgery. A second curvature sensor is coupled to the first curvature sensor at one end and to a tool at the other end to inform the computer-assisted image guided surgery or therapy system of the position and orientation of the tool with respect to the patient's body. A system is provided that incorporates curvature sensors, a garment for sensing the body position of a person, and a method for registering a patient's body to a volumetric image data set in preparation for computer-assisted surgery or other therapeutic interventions. This system can be adapted for remote applications as well.

16 Claims, 7 Drawing Sheets

SYSTEM AND METHOD FOR AUTOMATIC SHAPE REGISTRATION AND INSTRUMENT TRACKING

CROSS REFERENCE TO RELATED APPLICATIONS

This application claims the benefit of co-pending U.S. provisional patent applications Nos. 60/174,343 filed Jan. 4, 2000 and 60/179,073 filed Jan. 31, 2000, both entitled System of Automatic Shape Registration and Instrument Tracking, which are both hereby incorporated by reference in their entirety,

FIELD OF THE INVENTION

This invention pertains to computer assisted surgery and/or therapy using medical imaging systems, such as computed tomography (CT), fluoroscopy and/or magnetic resonance imaging (MRI) for guidance, and more particularly to a fiducial reference system and position sensing.

BACKGROUND OF THE INVENTION

The concept of computer-assisted stereotactic methods effectively began in 1979. By 1996 it was generally accepted that volumetric stereotactic procedures were feasible including the use of stereotactically directed instruments with respect to pre- or intraoperative displayed images.

Computer assisted image guided stereotactic surgery is beneficial in the biopsy and ablation of primary brain tumors, benign and malignant, as well as in many other intracranial procedures using computed tomography, MRI, positron emission tomography (PET) and single photon emissions tomography (SPECT). It is especially useful in accurate localization of intracranial vital structures. The passive articulated arm has been shown to be useful in the resection of brain metastases. Surgical navigation is used in head and neck tumors, employing MRI and CT imaging. Stereotactic interstitial brachytherapy has been used for inoperable head and neck cancers, with a head holder used for immobilization. Brachytherapy, the insertion of an ablative radioactive material into an otherwise inoperable tumor, can be placed accurately and through a smaller incision using computer assisted image guided stereotactic surgery. Other uses include vaporization of tumor slice and MRI, digital angiography, and computer-resident stereotactic atlases. Such methods are particularly utilized in neurosurgical and otolaryngological procedures of the head and orthopaedic procedures of the pelvis and spine.

The insertion of pedicle screws for spine fusion procedures is enhanced by computer-assisted methods. At first, 3-D images from CT scans were used but these have been replaced by computer-assisted fluoroscopy. For the insertion of iliosacral screws for pelvic ring disruption, the use of CT images has been shown to be accurate and safe, and can be employed when conventional X-ray is not useful due to the presence of contrast media in the bowels, or anatomic variations resulting in a narrow passage for the screw.

An essential capability of and step in the use of computer assisted surgery is registering the computer system and the digitized CT or MRI image data set to the patient in a common frame of reference in order to correlate the virtual CT or MRI image with the actual body section so imaged. Image-to-instrument registration at its most basic level requires some fiducials distributed in 3-dimensional space to be preoperatively imaged simultaneously with the patient. These fiducials provide an image frame of reference (ImFOR). The fiducials can either be synthetically added or consist of a set of pre-existing anatomical landmarks. There are three current methods of registering the data set of CT or MRI images of the object body segment to the actual body segment in the operating suite.

One method of registration uses CT or MRI imageable-markers or "fiducials" that can be recognized in renderings of the data set and also on the object body segment, and by touching or matching them point-to-point with a digitizing probe. Just before and during an operation, digitizing probe with sensors or emitters or reflectors for a waveform tracking system is then touched to each fiducial, enabling a computer to match the fiducials with the same points identified on the reconstructed images, planar and/or three dimensional, on a computer workstation. After a plurality of such fiducial points are matched, the computer program determines if an accurate match is obtained. This manual registration procedure locates the fiducials relative to an instrument frame of reference (InFOR). It is typical to use the operating room as the primary frame of reference (ORFOR) with the InFOR having a measured offset within the ORFOR. Thus the anatomy is registered to the image. This method is referred to as point-to-point registration.

A related registration method using fiducials attached to the patient involves mounting a reference frame directly to the patient's skeleton, such as the spine, pelvis or femur. In some instances, the skull can be fixed to a table mounted frame. The position of this frame of reference is optically tracked in real-time using the same video cameras used to track the surgical or therapeutic instrument. With the fiducials' physical location being known relative to the InFOR and the InFOR being known relative to the ORFOR and the fiducials also being known relative to the image, the location of arbitrary points in the image can be located in the physical space. Mathematically there is a bilinear transformation between the two spaces and an isomorphism exists, so operations in one space accurately reflect operations in the other. The instrument is then tracked (passive navigation) using one of several methods.

A second method of registration involves touching a segment of the body multiple times with a digitizing probe to obtain a multitude of points that will give a surface or shape that can be matched with the anatomic shape. Another version of this method uses an ultrasound probe with sensors, emitters or reflectors to map the surface of underlying bone to obtain a shape or surface. The computer program then matches the shape of the combined points to match the reconstructed image of the object part of the body. This method is referred to as shape or surface matching registration.

A third method of registration involves taking an X-ray of the body segment with a digitizing fluoroscope and matching the two-dimensional images with the three-dimensional data set.

The first registration methods require the surgeon to place fiducials on or in a patient before an imaging study and then use a digitizing probe to touch point fiducials or a surface, which is a tedious process. Using anatomic fiducials to register vertebrae for the insertion of pedicle screws has proven tedious and time consuming, so much so that this method has not gained general acceptance by orthopedic surgeons. The second method requires the exposure of a large area of bony surface in some cases, which is contradictory to one of the aims of using small incisions. The third method is more automatic but requires that a portable X-ray fluoroscopy machine be used.

Image to patient registration has been performed cutaneously by attaching spheres to a patient's scalp and then intraoperatively imaging these spheres using an ultrasonic sensor. Direct ultrasonic registration of bony tissue with their CT images is being developed.

A key component in any IGT/IGS system is the 3-dimensional (3-D) instrument tracker that informs the system computer of where the surgical or therapeutic instrument is and how it is oriented in 3-D space within the frame of reference. Currently there are four approaches to digitizing the position of the surgical or therapeutic instrument relative to some frame of reference: electromechanical; ultra-sonic; tuned, low-frequency, magnetic field transmitter source and a sensor-pointer; and infra-red optical.

An early approach to instrument tracking borrowed technology from robotic manipulators. These systems use articulated arms with optical shaft encoders or angle potentiometers to measure the angular displacements of each of the joints. Such measurements were combined to provide a mathematical estimate of the instrument's position and orientation. However, electromechanical passive articulated arms present several disadvantages that have limited their use, including: limited working volume due to constraints on arm weight; difficulties in moving free objects due to joint friction; positional accuracy limitations; the need for multiple manipulator arms in many situations; the inability to detect erroneous readings made by optical encoders at one or more joints; and difficulties associated with sterilizing or draping the large articulated arms.

Ultrasonic digitizers utilizing time-difference of arrival techniques have been used to locate instruments, but with limited success due to their: sensitivity to changes in the speed of sound; sensitivity to other operating room noises and echoes; and unacceptable accuracy in large operating volumes.

Magnetic field tracking of instruments has been tried, but suffered from operational difficulties caused by interfering fields associated with nearby metal objects and unacceptable positional accuracy for surgical or therapeutic use.

SUMMARY OF THE INVENTION

According to one aspect of the present invention, there is provided a surgical or device for performing surgery or therapeutic interventions on a patient, comprising a first curvature sensor configured to be placed on the patient, an attachment fixture attached to the first curvature sensor, a computer electronically coupled to the curvature sensor, a plurality of fiducials capable of being detected by a medical imaging system, a second curvature sensor electronically coupled to the computer, the second curvature sensor having a first end and a second end and capable of being coupled to the attachment fixture at the first end, and a tool connector coupled to the second end of the second curvature sensor.

According to another aspect of the present invention, there is provided a surgical device for performing surgery or therapeutic intervention on a patient comprising an attachment fixture, at least one fiducial capable of being detected by a medical imaging system, a curvature sensor coupled to the attachment fixture at one end and coupled to a tool connector at the other end, and a computer electronically coupled to the curvature sensor.

According to another aspect of the present invention, there is provided a device for use in an image guided therapy or image guided surgery system comprising a curvature sensor configured to be applied to a patient, an attachment fixture coupled to the curvature sensor, and a plurality of fiducials coupled to the curvature sensor.

According to another aspect of the present invention, there is provided a device for generating a frame of reference for an image guided therapy and image guided surgery system, comprising a curvature sensor configured to be applied to a patient, an attachment fixture and at least one fiducial.

According to another aspect of the present invention, there is provided a device for generating a frame of reference for an image guided therapy and image guided surgery system, comprising a ribbon comprised of one or a combination of plastic, metal wire, metal strip, fabric, rubber, synthetic rubber, nylon, thread, glass, or paper, a plurality of fiducials attached at known inter-fiducial distances along the ribbon, and an attachment fixture coupled to the ribbon at a known position with respect to the plurality of fiducials.

According to another aspect of the present invention, there is provided a sensing mesh, comprising at least one curvature sensor, a plurality of filaments coupled to the plurality of curvature sensors, a plurality of fiducials coupled to the curvature sensor(s) or to the plurality of filaments. In a further embodiment of this aspect, the sensing mesh is configured as a garment, such as a cap or as a garment to fit a human pelvis or torso.

According to another aspect of the present invention, there is provided a system for monitoring or enabling surgery or therapeutic intervention on a patient at a distance, comprising a first curvature sensor configured to be placed on the patient, an attachment fixture attached to the first curvature sensor, a computer electronically coupled to the curvature sensor, a second curvature sensor electronically coupled to the computer, the second curvature sensor having a first end and a second end and capable of being coupled at the first end to the attachment fixture, a surgical tool capable of being coupled to the second end of the second curvature sensor, and a communication device electronically coupled to the computer.

According to another aspect of the present invention, there is provided a device for monitoring the motions of a body, comprising a garment configured to be worn by a body, the garment including at least one curvature sensor(s) and a plurality of filaments coupled to curvature sensor(s) to form a mesh, and a communication device coupled to the curvature sensors and configured to communicate the output of the curvature sensors to a distant receiver.

According to another aspect of the present invention, there is provided a method of locating fiducials within a CT or MRI image of a patient comprising the steps of placing an array of fiducials on the patient, each fiducial within the array being located at known inter-fiducial distances apart, imaging the patient, identifying and locating in the image a reference point on the array of fiducials, inspecting the image one inter-fiducial distance from the reference point and identifying a fiducial using an image recognition means, inspecting the image one inter-fiducial distance from the last identified fiducial and identifying a fiducial using an image recognition means, and repeating the last step until all fiducials are located.

According to another aspect of the present invention, there is provided a method of registering a patient to an image from a CT or MRI system, comprising the steps of placing a curvature sensor on the patient, the curvature sensor being coupled to at least one fiducial, imaging the patient using a CT or MRI imaging system to produce an imaging study, analyzing the imaging study to create a volumetric data set in a computer database, the data set including identification of the at least one fiducial and the curvature sensor, electronically connecting the computer to the curvature sensor, determining the three-dimensional shape of the curvature sensor by using the computer to analyze the signal produced by the curvature sensor, and correlating the volumetric data set in the computer database to the three-dimensional shape of the curvature sensor by identifying the position of the at least one fiducial as a common point in a frame of reference.

According to another aspect of the present invention, there is provided a method for conducting surgery on a body, comprising the steps of placing a first curvature sensor on the body, the first curvature sensor having at least one fiducial in a known position with respect to the first curvature sensor, conducting an imaging study of the body using a CT or MRI system, the imaging study recording the position of the at least one fiducial with respect to the body, processing the imaging study to create an image data set and storing the image data set in a computer, the data set including the position of the at least one fiducial with respect to the body, connecting the first curvature sensor to the computer and using the first curvature sensor information to register the first curvature sensor and the at least one fiducial to the image data set, coupling one end of a second curvature sensor to the body at a known position and orientation with respect to the at least one fiducial and coupling a surgical tool to the other end of the second curvature sensor, displaying an image of the body from the image data set superimposed with an image of the position and orientation of the surgical tool with respect to the body; and using the superimposed image of the surgical tool on the image of the body to guide the surgical tool.

DETAILED DESCRIPTION OF THE PREFERRED EMBODIMENTS

Figure 1:
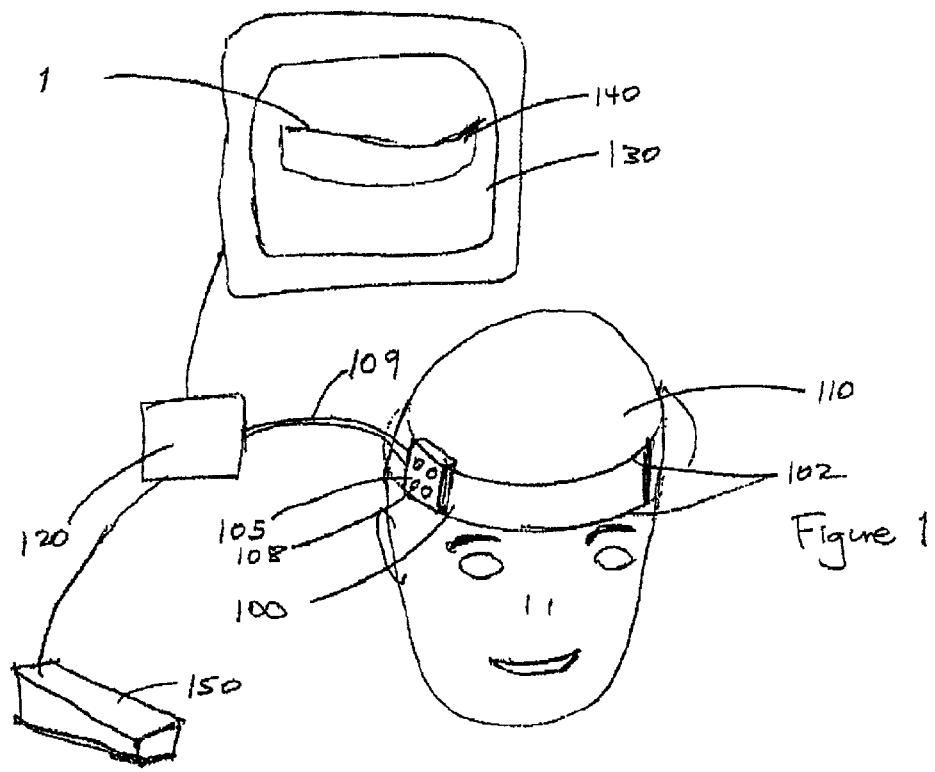
FIG. 1 is a perspective view of an embodiment of the invention positioned on a human head.

The present inventors have realized that the disadvantages of current image guided therapy and image guided surgery (IGT/IGS) systems may be reduced or eliminated by combining curvature sensors to generate an attachment fixture-centered frame of reference for the therapy or surgery system. Curvature sensors are able to precisely measure curvature and output electronic signals encoding their curvature in three-dimensional space with at least one imaging sensor observable position reference marker or fiducial. One or more curvature sensors, as described herein, may be applied to the skin of a patient to electronically measure, in real-time, the precise contour of a portion of the patient's body and provide this three-dimensional surface contour data to a computer where such data may be correlated with a volumetric image data set obtained from a CT or MRI imaging study of the patient. Attaching a positional reference fiducial marker to the curvature sensor(s) at a known position with respect to the curvature sensor(s) permits the curvature sensor to be located in a CT or MRI imaging study in three-dimensional space. With at least one fiducial point located in the imaging study data set and on the curvature sensor, the computer of an image guided therapy or image guided surgery system can easily register (i.e. dimensionally correlate) the data set to the real-time surface contour measurements to create a correlated frame of reference for monitoring the position of a tracked instrument with respect to the patient. With the images thus correlated, the computer generates an image that superimposes the position and orientation of the surgical instrument on the correlated volumetric image of the patient drawn from the imaging study data set. Thus, near-automatic registration of the patient to the image study data set may be accomplished intraoperatively, even when the patient is moved during therapy or surgery.

The inventors further realized that by coupling one end of a second curvature sensor to the patient at a known place in three-dimensional space, such as at or near the positional reference fiducial marker or the first curvature sensor, and coupling a surgical instrument to the other end of the second curvature sensor, the position and orientation of the surgical or therapeutic instrument can be registered to the patient and the imaging study data set intraoperatively in real-time. Using a second curvature sensor, anchored or coupled to a registerable known position on the patient, to track the surgical or therapeutic instrument enables a computerized image guided therapy or image guided surgery system that does not require an optical tracking or electromechanical tracking system. Eliminating optical and electromechanical tracking, eliminates the problems and cost associated with such devices. The resulting computer aided therapy or computer aided surgery system according to one embodiment of the present invention comprises at least one fiducial reference point attached to a first curvature sensor for measuring the surface shape of a portion of a patient and/or a set of physically constrained fiducials for computing the surface shape of a portion of a patient, a second curvature sensor configured to hold a surgical or therapeutic tool or instrument on one end and to be attached at the other end to a known position with respect to the fiducial reference point or the first curvature sensor (e.g. fastened to the fiducial reference), and a computer system with software configured to determine the three-dimensional positions of the first and second curvature sensors, to register those positions with respect to an image data set, and to display the image and surgical or therapeutic tool in the same frame of reference for use as a guide for the doctor or therapist.

Curvature sensors, as used herein, include any sensor or combination of sensors whose function is to measure the curvature of a linear element in three-dimensional space with respect to a reference point, such as a fixed end, and output a digital signal that communicates the measurements to a computer. The linear element of a curvature sensor may be in the form of a fiber, fiber optic, cable, bundle of fibers, strip, tape, or band, and, as is described in greater detail herein, a plurality of linear elements may be coupled to interconnecting filaments to form a flexible mesh that will measure the 3-D shape of a surface or manifold. The curvature sensor may also comprise an electronic interface device for receiving measurement signals from the sensor's linear element and transforming such measurement signals into a digital signal output readable by a computer. As used herein, the term "curvature sensor" may encompass such an electronic interface device.

One curvature sensor that is suitable for use in various embodiments of the present invention and is illustrated in the drawings relies on linear, bipolar modulation of light throughput in specially treated fiber optic loops that are sealed in absorptive layers. This fiber optic curvature sensor consists of paired loops of optical fibers that have been treated on one side to lose light proportional to bending of the fiber. The lost light is contained in absorptive layers that prevent the interaction of light with the environment. An electronics interface box attached to the fiber optics illuminates the loops, measures return light, encodes the measurements and relays information to a computer having software that calculates the 3-D instantaneous shape of the sensor. Using this information, the computer is able to generate a 3-D model of the sensor and display a graphic image of the sensor's linear element on a computer screen. The fiber optic type curvature sensor is disclosed in U.S. Pat. Nos. 5,321,257 and 5,633,494 issued to Danisch, the specifications of which are hereby incorporated by reference in their entirety. A commercial version of the curvature sensor is produced by Measurand Inc. (New Brunswick, Canada), comprising a flexible, fiber-optic linear element that provides position measurements of the entire length and shape of the tape including its endpoint. Position determination is accomplished by the electronic processing of light signals transmitted down the fiber optic cable. Since the curvature sensor uses internally sensed fiber optic cables to determine their position, the sensor can be made of little more fiber-optic fibers surrounded by an absorptive layer, reducing the interconnections between the patient's frame of reference and the instrument to a non-interfering, extremely low-inertia, highly flexible, thin encapsulated glass fiber that is easily sterilized and may be made to be disposable.

While such a fiber optic curvature sensor is illustrated in the figures and referenced herein, other types of curvature sensors may also be used and are contemplated as part of this invention. For example, other curvature sensors may employ: conductors whose electrical resistance varies when bent, such as strips of conductive polymers, or flexible strips of semiconductor or metal oxide materials; conductive wires covered by insulator material whose insulation properties vary when subjected to bending stress; or flexible cables, such as special co-axial cables, whose inductive or capacitive properties vary when the cable is bent (e.g. by reducing the gap between a central conductor and one or more surrounding conductors). As with the fiber optic curvature sensors described herein, electrically-based curvature sensors would employ a pulsed or oscillating current and an electronic interface/detector to locate the distance along the sensor to a bend, the amount of bend and direction of a bend in two-dimensions, and output this information in a form readable by a computer. With several alternative types of curvature sensors useable, the term curvature sensor should be understood herein as encompassing any sensor capable of performing the functions of measuring the three-dimensional position of the length of a linear element, either continuously or at intervals (i.e. points along the linear element) with respect to a reference point (e.g. an end or mid point), and providing an output signal that can be read by a computer, including sensors that employ an intermediary electronic interface device to produce a computer-readable output, such that the computer can determine the 3-D positions and orientations of the linear element along its length.

A curvature sensor need not be a physical device which determines its own position in 3-D space, but can also include a set of physically constrained fiducial points which are capable of being imaged. The physical constraints interconnecting the fiducial points can be used to aid in the automatic detection and localization of the fiducial points in the image as well as be used for the piecewise-linear (wire-frame) representation of the curvature of the surface which carries the fiducial points.

The term "fiducial" as used herein refers to anatomic or anatomically-fixed landmarks recognizable by an imaging system and used to locate known points with respect to a frame of reference, and more particularly to radioopaque (i.e. CT-visible) or MRI-visible markers applied to the skin surface overlying the site of an operation or attached to the underlying bone. Fiducials may be radioopaque spheres (e.g. lead, tungsten, or titanium spheres) for CT-imaging or fatty vitamin pills for MRI imaging, for instance.

The term "attachment fixture" as used herein refers to any fixture that is imageable and whose position is accurately known with respect to a set of fiducials and/or a curvature sensor. The function of the attachment fixture is to provide a known point of reference for the fiducials and curvature sensors that can be correlated to the imaging study data set when the patient and data set are registered. The attachment fixture may be as simple as an easily-recognized CT or MRI imageable feature on a garment, bandage, tape, band, wrap, screw or other patient-attachment item. In a preferred embodiment, the attachment fixture is both an easily recognized fiducial at a known position with respect to an array of fiducials on a curvature sensor mesh, and a hard-point for attaching one end of the second curvature sensor to a known 3-D position with respect to the patient so the IGT/IGS can determine the position of the surgical or therapeutic tool with respect to the patient at the other end of the curvature sensor. In this embodiment, the attachment fixture comprises a fiducial, a clip securing one end of the curvature sensor in a known position and orientation, and a means for mounting the attachment fixture on the patient, such as being sewn, stapled or glued to a garment to be worn by the patient. In another embodiment disclosed herein, the attachment fixture is simply an easily recognizable fiducial that is at a known position with respect to the other fiducials, such as a radioopaque metal (e.g. lead, tungsten or titanium) cross attached (e.g. sewn or glued) to a garment comprising an array of fiducials. The clip or latching mechanism for attaching one end of the curvature sensor may be any suitable physical interconnect that will hold one end of the curvature sensor linear element securely in 3-dimensions with a fixed orientation, including a spring clip, threaded connection, clamp, tongue-in-groove connection, or cylindrical cavity with a detent for receiving a grooved rod. Preferably, the clip will permit easy connect and disconnect of curvature sensors to enable patient preparation, sterilization of instruments, movement of the patient, etc. The attachment fixture may be disposable or of a more permanent nature. There may be more than one attachment fixture provided in a particular embodiment. The attachment fixture may provide for attaching a plurality of curvature sensors to the fixture simultaneously. And the attachment fixture may be integrated with other elements of the various embodiments, including, but not limited to, a garment comprising an array of fiducials, a curvature sensor, a curvature sensor garment, an electronics interface device for the curvature sensors, a patient restraint, a medical device holder or positioner, the operating table, a patient monitor (e.g. temperature, blood pressure or pulse monitor), or any combination of devices that will be placed in a fixed position and orientation with respect to the patient during imaging studies and the treatment/operation.

The term "medical imaging system" as used herein refers to any imaging capability, device or system capable of obtaining an image of a body, preferably a volumetric image, including without limitation computed tomography (CT), fluoroscopy, magnetic resonance imaging (MRI), positron emission tomography (PET) or single photon emission tomography (SPECT).

The terms "tool" and "surgical or therapeutic tool" as used herein refers to any device used in a surgery or therapy, including without limitation any instrument, probe, drill, scalpel, stent, suture, tool, scissors, clamp, or imager (such as a fiberscope). In embodiments not related to medical or therapeutic applications, the term "tool" refers to any device that aids the operator in accomplishing a task, including without limitation any probe, drill, wedge, imager, screwdriver, pick, scissors, clamp, wrench, key or other tool.

In a first embodiment of the present invention, an IGT/IGS system is provided employing a first curvature sensor to measure the shape and orientation of a portion of a patient's body, at least one fiducial to enable registration to an imaging study data set, a second curvature sensor configured to hold and track an instrument (e.g. a surgical instrument or probe), a computer to receive the three-dimensional information from the first and second curvature sensors and calculate therefrom their positions and orientations with respect to a frame of reference and register their positions to an imaging study data set, and a computer monitor for displaying the correlated images of the instrument, the patient and the imaging study data set. Using a second curvature sensor to track the position of the instrument enables an IGT/IGS system that measures instrument position directly instead of indirectly as with an optical tracking system. The CT or MRI imaging study data set is obtained with the first curvature sensor device fixed in place (such as with adhesive) on the object portion of the patient's body and imaged simultaneously with the anatomy. The flexible curvature sensor may be in the form of a strip, tape, band or mesh, as described herein, that can be laid upon or wrapped about the patient in the area where surgery is to be performed. CT or MRI readable fiducials may be incorporated within the curvature sensor strip, tape, band or mesh containing the curvature sensor(s), such as at set distances apart (forming an inter-fiducial distance). The relationship of the curvature sensor is thus established in relation to the anatomy seen on the imaging study. In surgery, a second flexible fiber optic curvature sensor device is physically attached at one end to the first curvature sensor, or to a structure that provides a known positional reference point for determining the location and orientation of the end of the second curvature sensor in 3-D space, such as an attachment fixture. In a preferred embodiment, the attachment fixture itself is imageable on the CT or MRI scan, or incorporates an imageable fiducial, so that its frame of reference position is established in the imaging study, thereby providing a known position for the end or origin of the second flexible fiber optic curvature sensor. The attachment device may be separate from or integrated with an electronics interface device that electronically couples the curvature sensor to the computer system. The second curvature sensor device is electronically linked to the computer system either directly or through an electronic interface device, which may be the same electronic interface device coupled to the first curvature sensor or a separate electronic interface device. This second curvature sensor has attached at its other end (i.e. the end not attached to the attachment fixture) a tool connector or holder for holding the surgical or therapeutic tool, instrument or probe to be used in the surgical or therapy procedure. The tool connector may be any structure or mechanism suitable for securely holding a tool, instrument or probe in a fixed orientation with respect to the end of the second curvature sensor, including any one of or a combination of a clasp, slot, opening, flange, or threaded member. The 3-D position of the second curvature sensor, particularly the location and orientation of the tool connector at its end, is measured or calculated in relation to the known reference point on the patient's body, which is registered in the computer system to the imaging study data set and the first curvature sensor which informs the computer of the position and orientation of the object part of the patient's body. Thus, the tool or surgical instrument is tracked and its position and orientation is determined by the computer system in relation to the object anatomy as recorded in the imaging study.

In an alternative of this embodiment, the second curvature sensor coupled to a tool holder for holding a surgical or therapeutic instrument or probe is used in an IGT/IGS system that retains an optical tracking system, with the positional information generated by the second curvature sensor used to supplement the instrument tracking provided by an optical tracking system in order to improve tracking accuracy and/or to provide continuity of instrument tracking when an object, such as the physician's body, blocks the lines of sight between the optical trackers and the instrument or probe.

This first embodiment may be understood with reference to FIGS. 1 through 7.

Referring to FIG. 1, a flexible fiber optic curvature sensor 100 is applied with adhesive to a human head 110. At one end of the curvature sensor 100 is an electronic interface box 105 that transmits, via a cord 109 to a computer 120, the information that specifies the shape of the curvature sensor 100. The light quantity is measured in the electronic interface box 105. The curvature sensor 100 has radioopaque or MRI visible fiducials in the form of bands 102 on each side of the head 110. Atop the electronic interface box 105 is attached a light emitting diode (LED) array 108. The LED array 108 is tracked by a camera 150 attached to the computer 120. The position of the electronic interface box 105, the curvature sensor 100 and the head 110 can be tracked by the computer 120 in all six degrees-of-freedom (DOF). The graphic shape 140 of the curvature sensor 100 is displayed on a computer monitor 130. An outline 142 of the graphic shape 140 corresponds to radioopaque/MRI visible bands 102.

Figure 2:
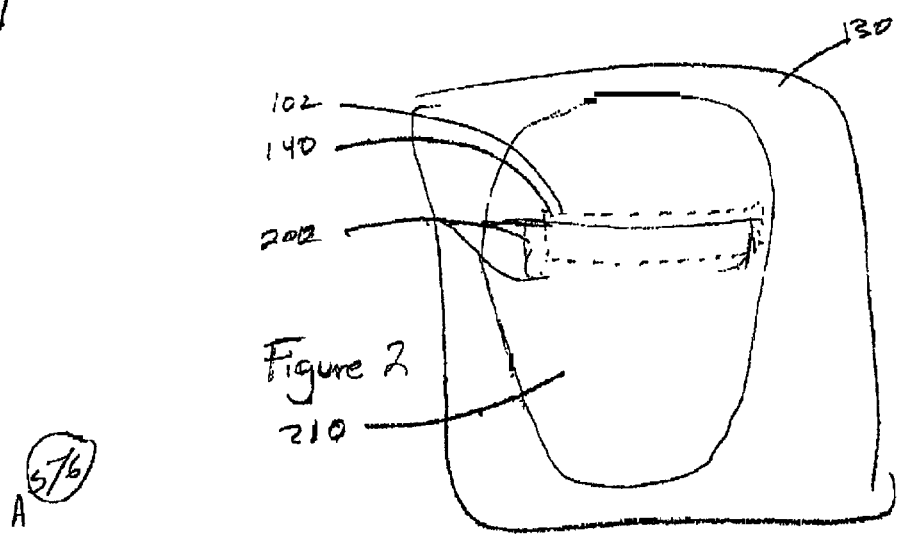
FIG. 2 is perspective view of a computer monitor showing graphic images.

Referring now to FIG. 2, a monitor 130 shows the three-dimensional reconstruction 210 of the head 110. Bands 202 are visualized on the reconstruction 210. The computer 120, using shape matching software, unites the fiducial bands 202 with the graphic shape 140 of the curvature sensor 100. The outline 142 of the graphic shape 140 is matched to radioopaque/MRI visible fiducial bands 102. As the position of the actual curvature sensor 100 has been determined by an optical tracking system of a camera 150 and a computer 120, relationships between the reconstruction 210 of the head 110 can now be made.

Figure 3:
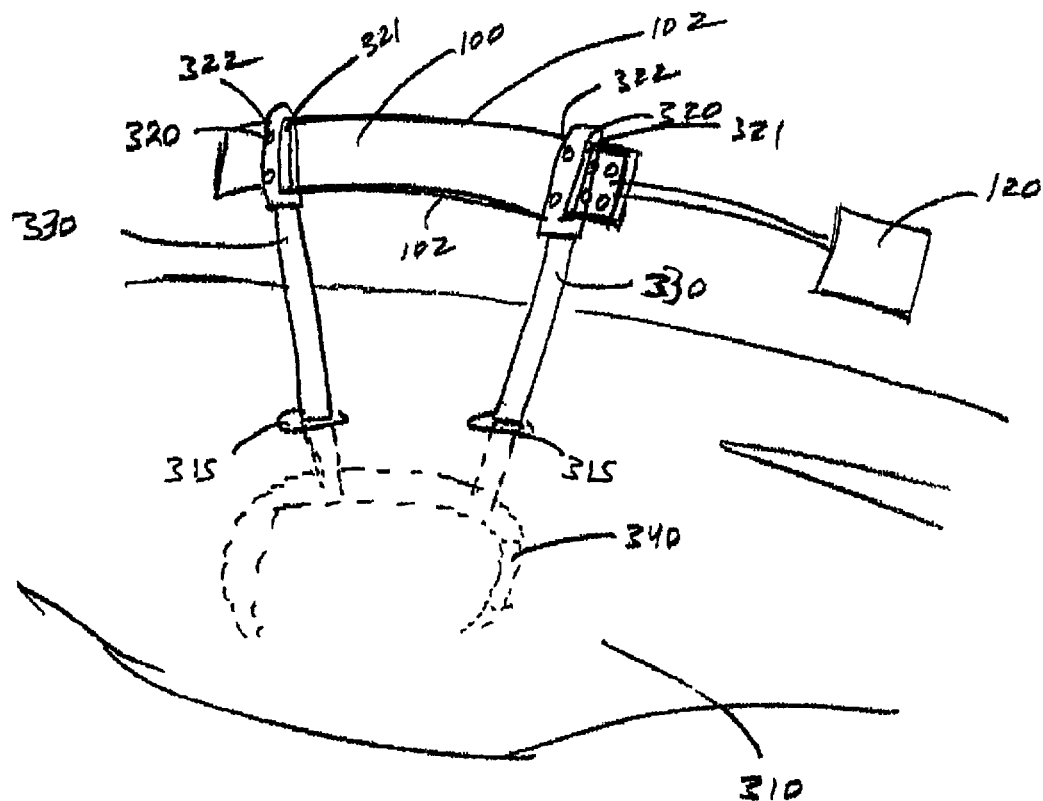
FIG. 3 is a perspective view of an embodiment of the invention attached to the ilium with metallic screws.

FIG. 3 shows an embodiment applicable to registration of a major bone. Large screws 330 are drilled into an ilium 340 illustrated in a human body 310. Caps 320 are placed over the screws 330. Each cap 320 has a slot 321 through which a flexible curvature sensor 100 is placed. Setscrews 322 hold the curvature sensor 100 firmly after it has been placed under tension through the slots 320. Setscrews 322 also hold the caps 320 firmly against the screws 330. Thus the curvature sensor 100 is held firmly in a fixed position in relation to the ilium 340. A CT scan is then performed that provides a digital data set of the pelvis 340 and the curvature sensor 100 in a fixed relation. The shape of curvature sensor 100 is seen in a reconstruction of the CT data, such as illustrated in FIG. 1, as provided by radioopaque fiducials or bands 102.

Figure 4:
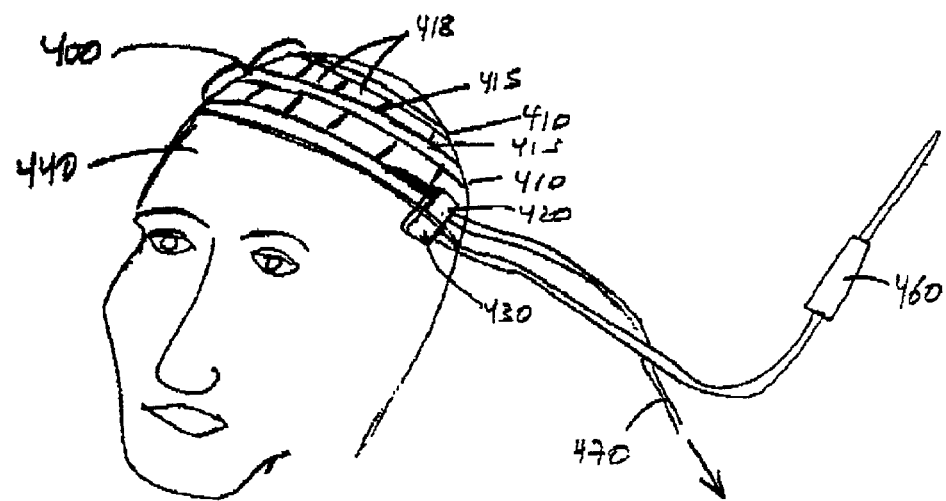
FIG. 4 is a perspective view of a human head with a cranial mesh embodiment and fiber optic curvature sensor attachment for tool tracking in accordance with an embodiment of the invention.

In FIG. 4, a cranial mesh 400 of flexible fiber optic curvature sensors 410 is held together with small connecting filaments 415, forming a cap on a head 440. An integrated electronics interface box/attachment fixture 420 connects to a computer via cable 470 and attaches to a second flexible fiber optic curvature sensor device 430. The cranial mesh 400 is visualized on the CT scan of the head 440 and also by the graphic representation thereof. The two images are merged or superimposed so that a CT of the cranial mesh 400 is registered with the graphic representation of the cranial mesh 400. Thus, a graphic representation of a cranial mesh 400 is registered to a CT of the head 440. The graphic shape of a second flexible fiber optic curvature sensor device 430 is thereby registered to the CT of the head 440, and a surgical probe 460 is thus registered to the CT of the head 440. Spaces 418 between the flexible fiber optic curvature sensor devices 410 and filaments 415 permit room for a surgical probe 460 to be used in surgical operations on the head 440. Flexible fiber optic curvature sensor devices 410 are wired individually to an electronic interface box 420 so that one flexible fiber optic curvature sensor device 410 can be disconnected and moved if needed for positioning the surgical probe 460 without affecting registration.

Figure 5:
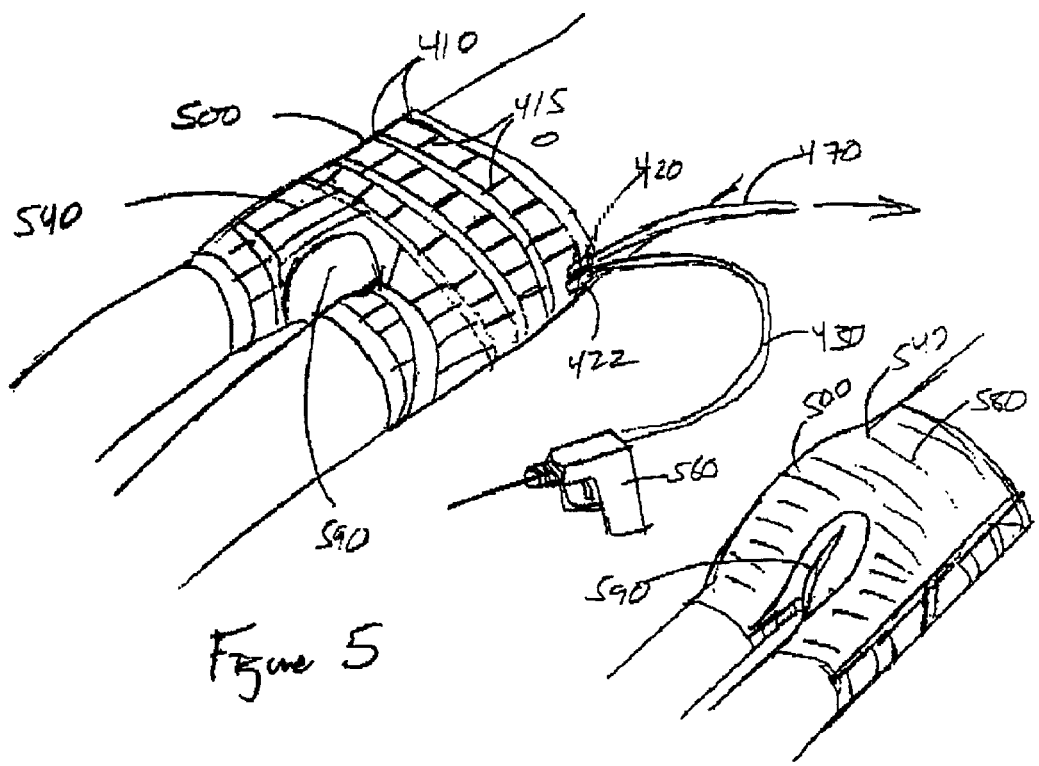
FIG. 5 is a perspective view of a pelvic region with a mesh embodiment and fiber optic attachment for tool tracking in accordance with an embodiment of the invention.

FIG. 5 illustrates a pelvic mesh 500 of flexible fiber optic curvature sensors 410 held together with small connecting filaments 415, forming a pants-like garment on a pelvis region 540. An electronics interface box 420 connects to the computer via a cable 470 and has an attachment fixture 422 where a second flexible fiber optic curvature sensor device 430 is attached. The pelvic mesh 500 is visualized on the CT scan of the pelvis region 540 and also by the graphic representation thereof. The two images are merged or superimposed so that the CT of the pelvic mesh 500 is registered with the graphic representation of the pelvic mesh 500. Thus, a graphic representation of the pelvic mesh 500 is registered to the CT of the pelvic region 540 and thus, more specifically, to the bony pelvis. The graphic shape of the second flexible fiber optic curvature sensor device 430 is therefore registered to the CT of the pelvic region 500, and a surgical drill 560 is thus registered to the CT of the pelvis 500. Spaces 418 between flexible fiber optic curvature sensor devices 410 and filaments 415 permit room for the surgical drill 560 to be used in surgical operations on the bony pelvis situated in the pelvic region 500. Flexible fiber optic curvature sensor devices 410 are wired individually to an electronic interface box 420 so that one flexible fiber optic curvature sensor device 410 can be disconnected and moved if needed for positioning the surgical drill 560 without affecting registration. The dorsal mesh 580 is elastic to provide a good fit onto the pelvic region 540. The pelvic mesh 500 has an open perineal section 590 for normal excretory functions.

Figure 6:
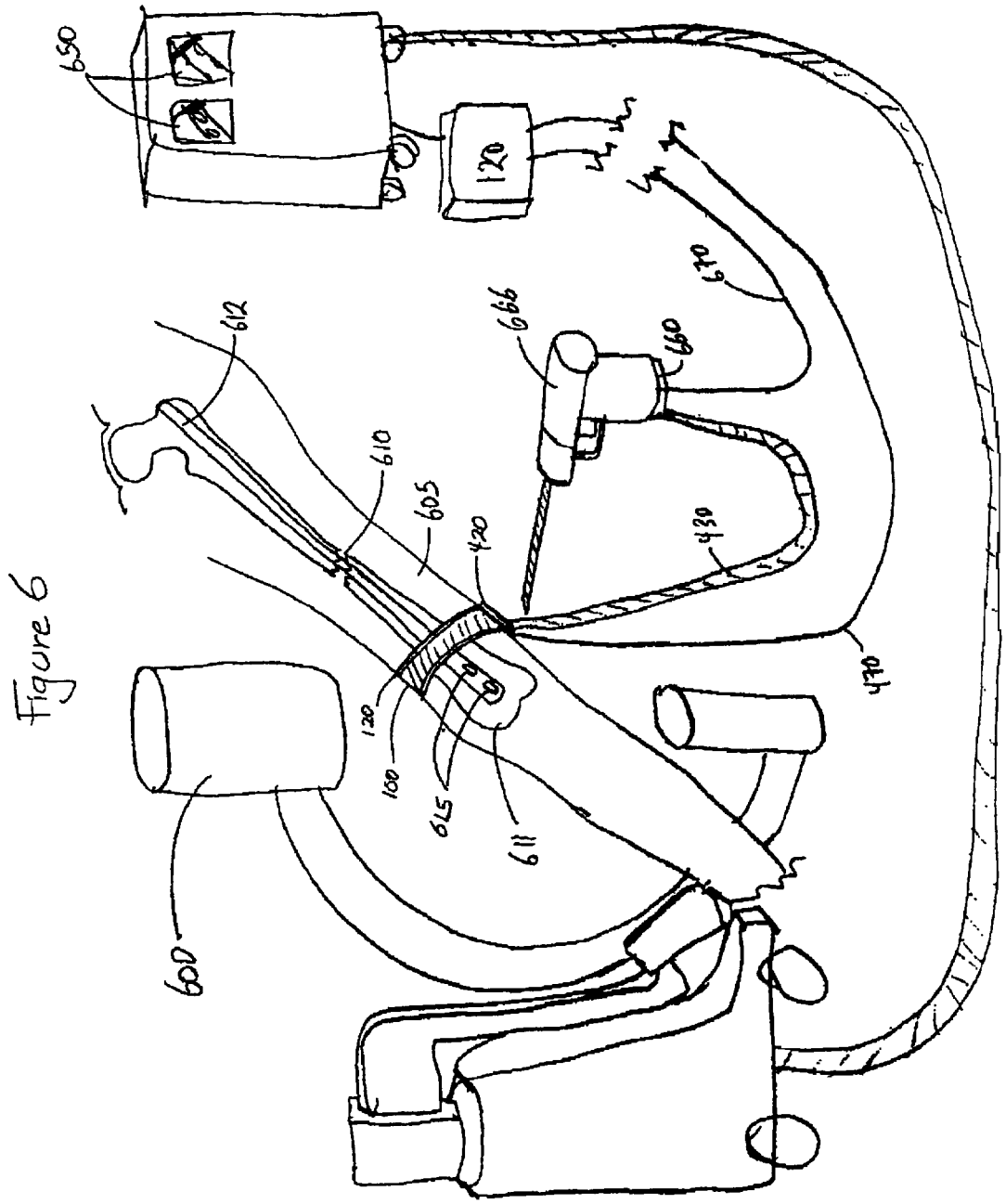
FIG. 6 is a system diagram of an embodiment of the invention applied in a surgery on a femur with an intramedullary nail.

Referring to FIG. 6, a flexible fiber optic curvature sensor 100 is applied with adhesive to the thigh 605. A fracture 610 of the femur 611 has been fixed with a intramedullary nail 612 without exposing the fracture site. A mobile fluoroscope 600 acquires two or more X-ray images 650 of holes 615 in the intramedullary nail 612. A computer 120 processes X-ray images 650 that include radioopaque markers 102 attached to the flexible fiber optic curvature sensor 100. An interface box 420 connects to the computer via a cable 470 and has an attachment fixture 422 with a second flexible fiber optic curvature sensor device 430 attached. A second interface box 660 attached to a drill 666 connects to the computer 120 with a second cable 670. The position of the second flexible fiber optic curvature sensor device 430 is more accurately determined as it is attached to the electronic interface box 420 at one end and to another electronic interface box 660 at the other end. Thus, the position of the drill 666 in relation to the holes 615 of the intramedullary nail 612 may be more accurately determined.

Figure 7:
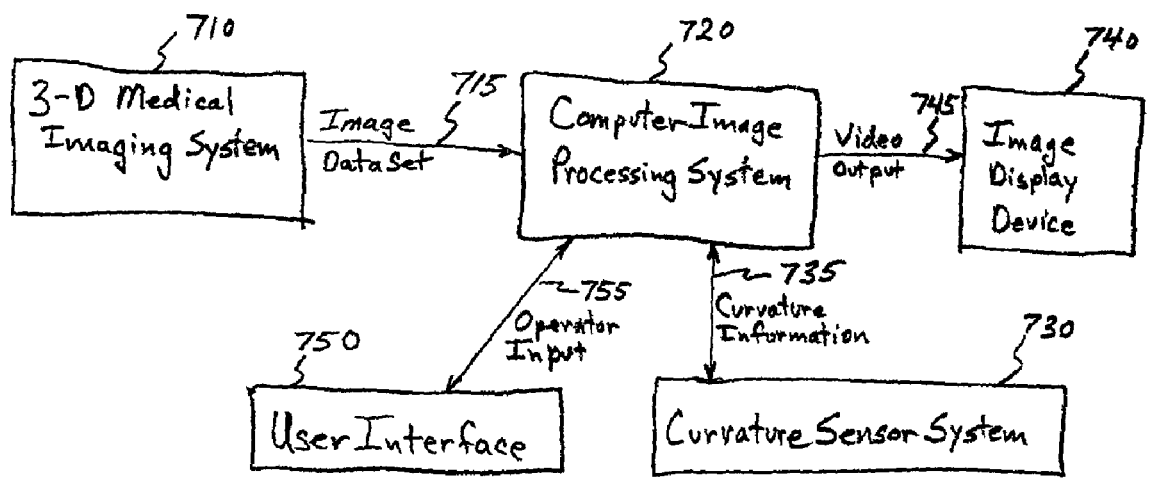
FIG. 7 is a system diagram of an image guided therapy/image guided surgery system in accordance with an embodiment of the present invention.

Referring to FIG. 7, an IGT/IGS system comprises the functional elements of a 3-D imaging system 710, a computer image processing system 720, a curvature sensor system 730, an image display device 740 and a user interface 750. The 3-D imaging system 710, which may be a CT or MRI imager, provides a volumetric image digitized data set 715 to the computer image processing system 720. The curvature sensor system 730 provides digitized information 735 on the 3-D position and orientation of the individual curvature sensors to the computer image processing system 720. The computer image processing system 720 correlates the image data set and the curvature sensor 3-D position information and provides a video output 745 to the image display device 740 that superimposes an image of the surgical instrument on the correlated volumetric image of the patient. Operator commands 755 is provided from the user interface 750 to the computer image processing system 720.

Figure 8A:
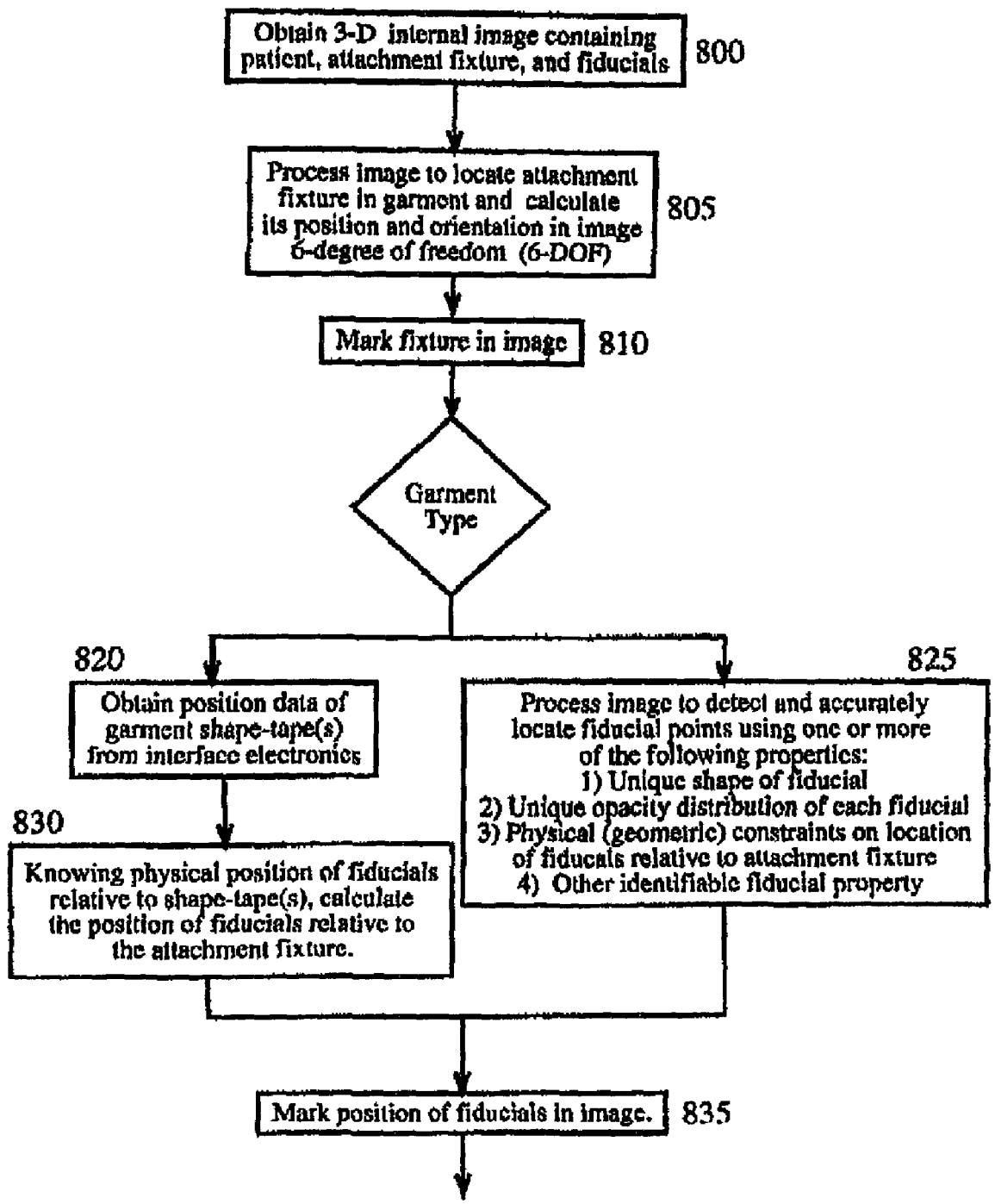
FIG. 8A is a flow diagram for producing an imaging study of a relevant portion of a patient wherein a 3-D internal image set is taken in preparation for pre-operative planning and intra-operative usage as per an aspect of an embodiment of the present invention.

The operation and method of using an IGT/IGS embodiment of the present invention may be explained with reference to FIG. 8A and 8B. Prior to the operation, the patient undergoes an imaging study (step 800) wherein a 3-D internal image set is taken of the portion of the patient's body that will be operated upon. In preparation for this imaging study, curvature sensor(s) (e.g. a curvature sensor garment), fiducials and/or an attachment fixture for the curvature sensor are applied to the patient, such as with adhesive so their positions on the body are recorded in the same imaging study. The imaging study data set is then processed (step 805) wherein the computer image processor locates the position of the attachment fixture with respect to the patient's anatomy, the fiducials and, if employed, the curvature sensor garment, and calculates their positions and orientations within the image data set. Next, (step 810) the attachment fixture is marked on the image data set.

As described herein, the IGT/IGS system may be employed with a curvature sensor (which incorporates fiducials) applied to the patient, or with only an array of fiducials applied to the patient with no curvature sensor on the patient. The operation of the system differs slightly as summarized in FIG. 8A.

If a curvature sensor is applied to the patient, the computer image processing system obtains the 3-D position information from the curvature sensor (step 820). Then the computer image processing system calculates the position of the attachment fixture relative to the fiducials (step 830) using the known relative positional information of the fiducials to the curvature sensor.

If a curvature sensor is not applied to the patient, the computer image processing system processes the image to detect and locate fiducials (step 825) based upon their shape, opacity, geometric position with respect to the attachment fixture (e.g. fiducials coupled in known locations in a garment coupled to the attachment fixture), or other image-recognizable property.

With the position of fiducials determined, the image data set is marked (step 835) to make them obvious to the user.

Figure 8B:
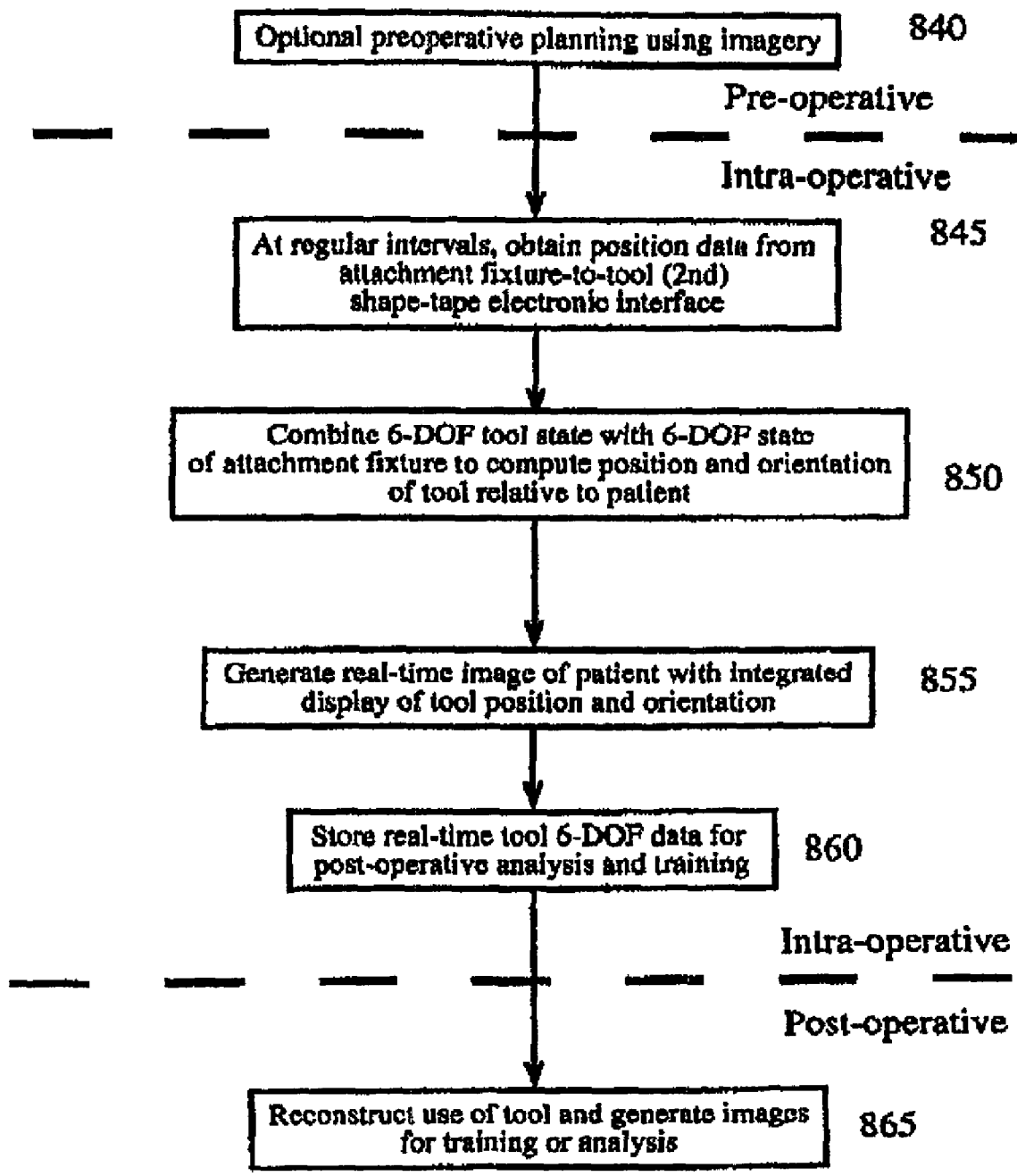
FIG. 8B is a flow diagram for utilizing the imaging study of FIG. 8A in pre-operative planning, intra-operative use, and post-operative analysis and reconstruction as per an aspect of an embodiment of the present invention.

Referring to FIG. 8B, the physician may plan the operation using the imagery (step 840), wherein cues, templates, guide markers or other visual clues may be provided to the computer image processor for display during the operation.

During the operation, the computer image processor will obtain positional information from the curvature sensors (step 845), such as via electronic interface device(s), on a near-real time basis. The computer image processor then uses the curvature sensor information and the imaging study data set, and in particular the location of the attachment fixture, to compute (step 850) the position and orientation of the surgical instrument relative to the patient. Using this position and orientation information, the computer image processor generates (step 855) a near-real time image of the patient with an integrated display of position and orientation of the surgical instrument. As the instrument position is displayed, the computer also records (step 860) the position and orientation of the surgical instrument in a computer database. This stored position/orientation information permits post-operative reconstruction (step 865) of the operation for analysis and/or training.

With a first curvature sensor affixed to the patient and a known reference point provided at the attachment fixture, this embodiment will enable establishing an attachment fixture-centered frame of reference. Since an attachment fixture-centered frame of reference may be divorced from the operating room coordinate system, this embodiment may be employed to accommodate movements of the patient or an extremity undergoing surgery without requiring extensive re-registration of the instrument or probe to the data set drawn from the image study. This capability would enable a surgeon to reposition a body or extremity during an operation if necessary without interrupting or delaying the procedure, or introducing positional errors into the IGT/IGS system. The direct connection between the patient and the instrument via a second curvature sensor also makes the system far more compact than video tracking systems.

An alternative embodiment IGT/IGS system uses a conventional optical tracking system to track the surgical instrument, but makes use of a curvature sensor, fiducials, and a computer workstation that synthesizes CT or MRI data into usable graphics to provide automatic registration of the object section of the body with the CT or MRI image data set. This embodiment allows the surgeon to guide instruments using the optical tracker, while alleviating several significant disadvantages of existing passive navigation systems for IGT/IGS systems.

In another embodiment of the present invention, a plurality of curvature sensor linear elements (e.g. encased optical fibers) are laid out in an array and held together with strong filaments to form a mesh or fabric of multiple curvature sensors. This embodiment is illustrated in FIG. 4 and 5.

Referring to FIG. 5, the curvature sensors 410 are positioned in parallel to each other and coupled to cross-running filaments 415 to form a mesh. The cross-running filaments may be any number of materials, including any one or combination of plastic, metal wire, metal band, polymer plastic, paper, cloth, nylon, rayon, segmented solid pieces of plastic, metal or wood, or similar formable material. The curvature sensors 410 are coupled to an electronic interface device 420 which sends curvature information to a computer (not shown) via cable 470.

The mesh or fabric may be shaped to conform to a targeted body part much like a garment, which may provide significant clinical advantages. For example, referring to FIG. 4, a cranial mesh garment 400 may be shaped like a cap to conform to a patient's head 440. In this embodiment, the curvature sensors 410 are aligned in parallel hoops or bands and held in place with filaments 415 configured in a radial pattern originating at the crown. As another example, the curvature sensor mesh may be configured as a pelvic garment 500 that is shaped much like a pair of bicycle shorts with a cutout 590 for the perineum, as illustrated in FIG. 5. The curved sensors 410 are provided on the exposed portion of the mesh while the patient is lying in bed, usually the anterior or ventral section. The dorsal or posterior portion may be an elastic band or mesh 580 to provide a better fit to the abdomen 540. The electronic interface device 422 attachments for the plurality of curved sensors 410 in the mesh may be at the edge or may be part of the attachment fixture 422, as illustrated in FIG. 5, and/or electronic interface device for a tool 560 tracking second curvature sensor 430, as is also illustrated in FIG. 5. The garment may comprise an array of fiducials at regular points in the mesh and a rigidly affixed attachment point or attachment fixture for securing a dynamic frame of reference (DFOR) to a patient.

In another embodiment, a fiber optic curvature sensor is attached to the surface of the patient by an adhesive, as may be appropriate in neurosurgical cases. In another embodiment, metal pins or screws attach the fiber optic curvature sensor to bone. In either embodiment, fiducial markers detectable by X-ray or magnetic resonance imaging, such as fiducials made of titanium, may be incorporated into the curvature sensor at known dimensions from a reference point, such as a set distance apart along a flexible wire or tape fixed or attached to an attachment fixture/reference fiducial, or at a set distance along fibers in a fabric, bandage or garment that is fixed or attached to an attachment fixture/reference fiducial. A sensor or emitter appropriate to the waveform tracking device employed may be attached to the device. A three-dimensional data set of the object body section is then obtained. This data set is then transferred to the computer workstation to be used in a surgical procedure.

In one embodiment, registration is accomplished automatically. During surgery, the computer ascertains the shape of the fiber optic curvature sensor, which has been positioned on the patient, using the information passed by the electronic interface device. The digitized shape of the curvature sensor is then matched with the shape that is evident in the imaging data set, such as determined by the positions of the fiducials incorporated within the curvature sensor. Registration can then be determined automatically without the surgeon needing to use a probe or direct the use of a fluoroscope.

In an embodiment appropriate for cranial procedures, the curvature sensor, with integrated fiducials, is placed completely around the head in a position such that it will not interfere with the anticipated place for surgical entry. The curvature sensor and fiducials assembly may be adhered to the skin surface, making it very stable and secure, thus assuring that the built-in reference frame remains in the same position. In this embodiment, the curvature sensor and fiducials may be in the form of a garment shaped like a cap, or may be in the form of a tape or bandage that is wrapped about the head.

Another embodiment of this invention comprises the use of a curvature sensor to provide two-dimensional image tracking using a fluoroscope. A fluoroscope obtains images of the object body section that has attached the flexible fiber optic curvature sensor device comprising radioopaque fiducial markers, which may be at set distances along a wire or at set positions within a grid. Thus, the position of the flexible fiber optic curvature sensor device is determined in relation to the object body section. Tracking of surgical tools in relation to the object body section is then accomplished by using an optical tracking system with LEDs attached to the flexible fiber optic curvature sensor device. Alternatively, tracking may be accomplished by attaching the tools to a second flexible fiber optic curvature sensor device, eliminating the need for the reference frame and optical tracking system. In either embodiment, once the initial set of X-ray images has been obtained, further X-rays are not needed as the relative position of the surgical tool to the object body is now recorded.

The present invention includes two embodiments associated with two registration options. One embodiment comprises a curvature sensor and fiducials affixed to a dynamic frame of reference (DFOR) wrap or garment. The other embodiment comprises only fiducials affixed to the garment with no curvature sensor. In both embodiments, a curvature sensor may be connected to the DFOR wrap or garment at an attachment fixture or fixture whose position is accurately known with respect to the wrap or garment frame of reference. This attachment fixture provides a physical and positional connection between the attachment fixture, which has been preoperatively volumetrically-imaged with the garment frame of reference, and the instrument. The physical interconnect provided by the attachment fixture allows for the continuous tracking of the 6-degrees of freedom state of the instrument without the need for extraneous optical or articulated arm instrument tracking equipment in the operating room. The instrument's kinematic state can then be displayed on a monitor viewable by the surgeon as a computer-generated image embedded in the preoperatively obtained volumetric image. There may be more than one attachment fixture provided on a curvature sensor mesh or garment. The attachment fixture may comprise a latching mechanism to physically attach one or more curvature sensors to a known reference point on the attachment fixture, and one or more fiducials which may be imaged with CT and/or MRI systems in order to establish the known position of the attachment fixture in the imaged frame of reference.

Since the entire fiber optic curvature sensor or other fiducials affixed to the garment are imaged, the coordinates of each fiducial are known in real-time, intraoperatively. More importantly, the position of each fiducials is known as the patient moves, such as in the process of breathing and expanding the chest. Since each fiducial's internal coordinates is known during the motion based upon information provided by the curvature sensor, this information can be used to provide a natural approach to warping images in real-time. Thus, a further embodiment of the present invention comprises a fiber optic curvature sensor-enabled garment which can dynamically track the movements of the fiducials on a patient's moving body. These tracked fiducial points can then be used to dynamically warp the preoperative image to more realistically present an image to the therapist as the patient motion is happening.

As a non-invasive alternative to registration methods, fiducials and a fiber optic curvature sensor may be affixed to a patient's skin, either adhesively or embedded in a garment, bandage, tape or other structure, at the time of volumetric pre-operative imaging. This garment is then left affixed to the patient for the duration of the treatment or surgery. The fiducials in the garment provide the image frame of reference as well as the attachment fixture for attaching an instrument connection fixture, also herein referred to as an attachment fixture, to a known reference point. The embedded fiber optic curvature sensors provide the dynamic garment frame of reference, not only in the sense of being affixed to the patient, but also in the sense that it can track, in real-time, the location of the fiducials. The real-time, intraoperative location of the fiducials can be used to synchronize the acquisition of instrument tracking data with the preoperative images for improved accuracy in certain dynamic scenarios such as therapy in the chest area.

Since the fiber optic curvature sensor is included in the volumetric image data set, its position is known relative to the image and it comprises a set of distributed fiducial points. Since the fiber optic curvature sensor measures its own position, a rigid attachment point provided by the attachment fixture can be part of the curvature sensor device or garment and used for the rigid attachment of a second curvature sensor whose other end is attached to a surgical instrument.

The first step in a general framework frame of reference registration is the definition of a relation among the different coordinate systems or, as used herein, frames of reference. Current methods include: reference preoperative images; fiducials; and instruments to a frame of reference affixed to the operating room. Assuming that the errors in establishing these relationships and their registration are independent, then the cumulative error, at least to a first approximation, is the root sum square of the individual errors in estimating these relationships. It is therefore clear that the methods and embodiments disclosed herein that will eliminate or reduce the number of frame registration steps will increase the accuracy of instrument positioning. It is also clear that calibration techniques can outperform registration techniques in terms of accuracy.

In addition to frame of reference registration problems, there is also a difficulty associated with the nonlinearities associated with CT, MRI, and other volumetric images. Originally, volumetric imaging was a visualization aid for surgeons and diagnosticians and nonlinearities in the image were relatively unimportant. When these same images are used for navigation, linearity becomes a significant issue. Such nonlinearities or distortion in computer aided surgical navigation with fluoroscopy have been recognized and correction methods have been developed. A second issue associated with the image itself is the spatial quantization of the image. Typically the image is digitally constructed from a series of slices or a helical scan of the patient. The fact that these individual slices have a finite thickness limits the number of samples taken on each fiducial. With a limited number of samples, the accurate estimation of the centroid of the fiducial can become problematic. For example, using a 5 mm sphere and 1 mm scan width yields only 5 spatial samples on the sphere, thereby limiting the accuracy that can be achieved in the image frame of reference (ImFOR) itself. In general, the methods of rigid-body transformations from one frame of reference to another are well known in the art. The difficulty is in accurately establishing the several frames of reference and their relations.

In an embodiment of the present invention that provides a dynamic patient-based frame of reference, these registration errors are significantly reduced by eliminating several registration procedures and exchanging them for one registration step and one calibration procedure. Furthermore, the calibration of the surgical instruments to the garment frame of reference can be done preoperatively, thus minimizing time in the operating room.

The direct connection between the patient and the instrument provided by the second curvature sensor eliminates the need for intraoperative video tracking and its associated equipment. Precise positioning of surgical instruments relative to 3-D CT and MRI (volumetric) and 2-D fluoroscopic images is important for the delivery of anti-cancer drugs, localized ablation of tumors, biopsy, and execution of pre-planned surgery. In the embodiment providing surgical instrument navigation, diagnostic and treatment modalities can be done easier and more cost effectively than current means allow. The ease of use of various embodiments of this invention will make it possible to precisely and repeatably place an instrument in particular positions at specified angles by therapists untrained in the details of its operation. This invention may significantly reduce patient morbidity, physician intraoperative difficulties, radiation exposure, and operating time, while at the same time improving repeatability of instrument placement, thus improving the accuracy of therapies and deliveries of medication. This improved accuracy will increase the information obtained from each set of experiments because of the repeatability of the procedures on the same or different individuals. Data on instrument position can also be recorded and associated with each operation to determine which instrument position provides the best effect, as well as for training of other therapists once the procedure is approved. These benefits are in addition to the elimination of the need for cumbersome operating room real-time optical tracking systems.

The use of this invention could be extended to vertebral biopsy and aspiration of the hip, which now requires an operating room environment with fluoroscopy. Using already obtained MRI data for herniated nucleus pulposis with radiculopathy, injection of corticosteroids around the nerve root could be facilitated. Other procedures requiring accurate needle placement would be more readily done.

Being less invasive and less cumbersome than current systems, this invention could be used in an out-patient setting, even in a physician's office, enabling precision procedures, such as percutaneous biopsy, to be done accurately and safely.

In an embodiment of the present invention, fiducials are positioned at known positions along a flexible fiber, such as a plastic or fabric ribbon, wire, metal band or plastic, fabric tape, that originates at a known reference position, such as an attachment fixture, and can be taped to or wrapped around a patient. As used herein, the term "ribbon" refers to a long, narrow flexible structure capable of fixing at least one fiducial in a known position along its length and being bent such as to conform to the contours or wrap about a body. The ribbon may be made of any material that is flexible or semi-rigid so as to be laid on top of or wrapped about a patient, including one or a combination of plastic, metal wire, metal strip, fabric, rubber, synthetic rubber, nylon, thread, glass (including fiber optic glass), or paper (as may be suitable for a pre-sterilized, disposable fiducial wrap). This embodiment significantly facilitates and enhances the registration of CT or MRI images since the fiducials are easily located by a computer because each fiducial is at a known dimension from the next. This reduces inaccuracies associated with using an intensity or threshold value determination of fiducials, which often results in false or missed fiducials since bodily tissues may result in images that are similar to those created by such fiducials. This embodiment enables a method of locating fiducials for an IGT/IGS system, comprising the steps of placing an array of fiducials on the patient, each fiducial within the array of fiducials being located at a known inter-fiducial dimension apart from one another, identifying and locating a reference point on the array of fiducials, such as an attachment fixture, inspecting the image one inter-fiducial length from the reference point and identifying a fiducial using an image recognition means, the identified fiducial becoming a last-identified fiducial, inspecting the image one inter-fiducial length from the last-identified fiducial and identifying a next fiducial using an image recognition means, the identified next fiducial then becoming a last-identified fiducial, and repeating the previous step until all fiducials within the array of fiducials have been identified in the image.

In a further embodiment of this invention, the curvature sensor garment is coupled to a communications device, such as a cable to a computer with an internet connection, a radio or cellular telephone data link, or a satellite communication data link, so that the positional and curvature information provided by the curvature sensors are communicated to a remote location. Such a garment and communication device would enable remote surgery or therapies. Such a garment and communication device would also allow the dynamic monitoring of a patient, such as while freely walking. This embodiment could have several useful applications for remotely monitoring the movements of athletes in training, patients engaged in physical therapy exercises, soldiers or rescue workers operating in adverse environments, or other applications where the precise, real-time position of body parts and/or tools they are using needs to be known.

Another embodiment comprising a communication device is a system for enabling remotely conducted or remotely monitored precision surgery. In this embodiment, a curvature sensor garment, mesh or fabric, with or without incorporated fiducials, is applied to a patient at a remote location, such as a battlefield medical facility. A data set of the injury is obtained using fluoroscopy or other means to create a digitized volumetric data set of the patient. A second curvature sensor is attached to the curvature sensor garment or fabric at an attachment fixture whose position is registered in the volumetric data set. The volumetric data set is communicated to another location, such as a hospital or a physician's office, where it is loaded on a computer. During surgery, the precise positional information on the patient's frame of reference, provided by the curvature sensor garment or fabric, and the precise location and orientation of a surgical tool, provided by the second curvature sensor, are communicated by the communication device to the distant location. In the distant location, a computer registers the volumetric data set with the patient's frame of reference and the position and orientation of the surgical tool, and displays the result on a computer monitor in the distant location. Using a verbal, video, telerobotic or other communication means, a physician at the distant location may then direct or observe the conduct of the remote surgery with greater confidence and precision than would be possible with only a video link between the two locations. This system may incorporate an IGT/IGS at the site of the remote surgery, but is not necessary.

The present invention offers several significant advantages over the state of the art. With this invention there is no exposure of additional bone for recording anatomical landmarks or percutaneous attachment of fiducials to bones, both of which require surgery in addition to that which is required for the required surgery or therapy. Intraoperative manual registration is not required because the instrument is directly connected to the patient's frame of reference by a curvature sensor which continually reports its position in 6-D space. The need for articulated mechanical arms or a frame containing multiple video cameras to reduce instrument blind spots is eliminated. The elimination of cumbersome tracking equipment reduces the sterilization problem to one of using disposable fiber optic cables which may attach between the patient's garment and the instrument. A small electronics interface box may be required as a part of the curvature sensor which can be easily draped since it is at one end of the curvature sensor. Since the position of the instrument is measured relative to a frame of reference which is affixed to the patient, patient movement ceases to be a problem. The physical interconnection between the patient and the instrument also reduces position estimation errors by replacing (intraoperative) registration steps with (preoperative) calibration.

Various embodiments of the present invention provide a device and method for an IGT/IGS system that is non-invasive, self-contained, passively-navigated, dynamically-referenced, and automatically image-registered, eliminating the need for the surgeon to do registration manually.

Numerous non-medicinal applications of the present invention are possible, including veterinary treatment/surgery systems, archeological research, explosive ordinance disposal and other applications where an imaging study is used to precisely guide a tool or device and there is a need for precise image registration and tool tracking or reconstruction of the physical motion of a tool or body part after the fact. This position and tool tracking data could be stored on a storage device associated with a personal computer worn by a person.

While the invention has been described in detail and with reference to specific embodiments thereof, it will be apparent to one skilled in the art that various changes and modifications can be made therein without departing from the scope of the invention. Thus, the breadth and scope of the present invention should not be limited by any of the above-described exemplary embodiments, but should be defined only in accordance with the following claims and their equivalents.

We claim:

1. A device for performing surgery or therapeutic interventions on a patient, comprising:
   a first non-invasive curvature sensor configured to be placed externally on a patient, the first non-invasive curvature sensor providing first external curvature data;
   imageable fiducials coupled to the first non-invasive curvature sensor; and
   an attachment fixture coupled to the first non-invasive curvature sensor; and
   a computer configured to receive the first external curvature data and relate the curvature of the first non-invasive curvature sensor to: the location of the imageable fiducials; and a 3-D internal image set of the patient.

2. The device of claim 1, further comprising:
   a second non-invasive curvature sensor providing second external curvature data, the second non-invasive curvature sensor having a first end and a second end and capable of being coupled to the attachment fixture at the first end; and
   a tool connector coupled to the second end of the second non-invasive curvature sensor.

3. The device of claim 2, further comprising a second attachment fixture capable of being positioned at a known location with respect to the first non-invasive curvature sensor, wherein the second end of the second non-invasive curvature sensor is coupled to the second attachment fixture and the tool connector is coupled to the second non-invasive curvature sensor between the first end and the second end.

4. The device of claim 2, further comprising a monitor for positionally displaying the tool connector with respect to the patient.

5. The device of claim 2, further comprising an optical tracking system electronically coupled to the computer and configured to positionally track the tool connector or a tool positioned in the tool connector.

6. The device of claim 5, wherein the computer uses both the second non-invasive curvature sensor and the optical tracking system to positionally track the tool connector or a tool positioned in the tool connector.

7. The device of claim 1, wherein the computer is configured to determine an attachment fixture-centered frame of reference based on the first external curvature data.

8. The device of claim 1, wherein the first non-invasive curvature sensor comprises a fiber optic curvature sensor.

9. The device of claim 1, wherein the attachment fixture comprises:
   at least one imageable fiducial; and
   a latching mechanism configured for attaching to the first end of the non-invasive second curvature sensor.

10. A device for performing surgery or therapeutic intervention on a patient, comprising:
    an attachment fixture;
    at least one imageable fiducial coupled to the attachment fixture, the imageable fiducial being capable of being detected by a medical imaging system;
    a non-invasive curvature sensor having a first end and a second end and capable of being coupled to the attachment fixture at the first end, the non-invasive curvature sensor configured to be placed externally on a patient, the non-invasive curvature sensor configured to provide external curvature data
    a tool connector coupled to the second end of the non-invasive curvature sensor; and
    a computer configured to receive the external curvature data and relate the curvature of the first non-invasive curvature sensor to: the location of the imageable fiducials; and a 3-D internal image set of the patient.

11. A device for use in an image guided therapy or image guided surgery system, comprising:
    a non-invasive curvature sensor configured to be applied externally to a portion of a patient, the non-invasive curvature sensor being adapted to measure and provide external curvature data;
    imageable fiducials located on the non-invasive curvature sensor;
    an attachment fixture coupled to the non-invasive curvature sensor, the attachment fixture comprising an imageable fiducial; and
    a computer configured to receive the external curvature data and relate the curvature of the non-invasive curvature sensor to: the location of the imageable fiducials; and a 3-D internal image set of the patient.

12. The device for use in an image guided therapy or image guided surgery system according to claim 11, wherein the non-invasive curvature sensor comprises a fiber optic curvature sensor.

13. A device for generating a patient based frame of reference for an image guided therapy or image guided surgery system, comprising:
    a non-invasive curvature sensor configured to be applied externally to a portion of a patient, the non-invasive curvature sensor being adapted to measure and provide external curvature data of the curvature of the portion of the patient;
    imageable fiducials coupled to the non-invasive curvature sensor; and
    an attachment fixture coupled to the non-invasive curvature sensor at a known position with respect to the non-invasive curvature sensor; and
    a computer configured to receive the external curvature data and relate the curvature of the non-invasive curvature sensor to: the location of the imageable fiducials; and a 3-D internal image set of the patient.

14. A device for generating a patient-based frame of reference for an image guided therapy or image guided surgery system according to claim 13, wherein each of the imageable fiducials are coupled to the non-invasive curvature sensor at known inter-fiducial distances.

15. A system for monitoring or enabling surgery on a patient at a distance, comprising:
- a first non-invasive curvature sensor configured to be placed externally on the patient, the first non-invasive curvature sensor providing first external curvature data;
- imageable fiducials coupled to the first non-invasive curvature sensor;
- an attachment fixture attached to the first non-invasive curvature sensor;
- a second non-invasive curvature sensor having a first end and a second end and capable of being coupled at the first end to the attachment fixture, the second non-invasive curvature sensor providing second external curvature data;
- a tool capable of being coupled to the second end of the second non-invasive curvature sensor; and
- a computer configured to:
  - receive the first external curvature data;
  - receive the second external curvature data;
  - relate the curvature of the first non-invasive curvature sensor to: the location of the imageable fiducials; and a 3-D internal image set of the patient;
  - provide an output of the curvature of the first non-invasive curvature sensor and the position and orientation of the tool coupled to the second end of the second non-invasive curvature sensor with respect to the attachment fixture; and
  - communicate the output of the computer to a distant receiver using a communication device that is electronically coupled to the computer.

16. A device for conducting surgery or therapy on a body, comprising:
- means for externally measuring the curvature of a body;
- means for locating the position of the means for externally measuring the curvature of a body within a frame of reference;
- means for determining the position of a tool with respect to the means for externally measuring the curvature of a body; and
- means for registering a 3-D internal image set of the body to the means for externally measuring the curvature of a body.

\* \* \* \* \*